(12) United States Patent
Hall et al.

(10) Patent No.: US 10,088,458 B2
(45) Date of Patent: Oct. 2, 2018

(54) STAGED PRECONCENTRATION AND PARALLEL COLUMN GAS CHROMATOGRAPHY

(71) Applicants: David R. Hall, Provo, UT (US); Dan Allen, Springville, UT (US); Steven Butala, Provo, UT (US)

(72) Inventors: David R. Hall, Provo, UT (US); Dan Allen, Springville, UT (US); Steven Butala, Provo, UT (US)

( * ) Notice: Subject to any disclaimer, the term of this patent is extended or adjusted under 35 U.S.C. 154(b) by 194 days.

(21) Appl. No.: 15/379,963

(22) Filed: Dec. 15, 2016

(65) Prior Publication Data

US 2018/0172647 A1 Jun. 21, 2018

(51) Int. Cl.
| | |
|---|---|
| *G01N 30/14* | (2006.01) |
| *G01N 30/16* | (2006.01) |
| *B01D 53/04* | (2006.01) |
| *G01N 30/08* | (2006.01) |
| *G01N 1/22* | (2006.01) |
| G01N 30/02 | (2006.01) |

(52) U.S. Cl.
CPC ......... *G01N 30/14* (2013.01); *B01D 53/0438* (2013.01); *G01N 1/2214* (2013.01); *G01N 30/08* (2013.01); *G01N 30/16* (2013.01); *B01D 2259/40088* (2013.01); *G01N 2030/025* (2013.01); *G01N 2030/143* (2013.01)

(58) Field of Classification Search
CPC ........ G01N 30/08; G01N 30/14; G01N 30/16; G01N 2030/085; G01N 2030/143; G01N 2030/025; G01N 30/20; G01N 1/2214; B01D 53/0438; B01D 2259/40088
See application file for complete search history.

(56) References Cited

U.S. PATENT DOCUMENTS

2009/0090197 A1* 4/2009 Finlay .................. G01N 1/2214
                                                         73/863.12

* cited by examiner

*Primary Examiner* — Robert Clemente

(57) ABSTRACT

We disclose a device that both extracts and preconcentrates volatile analytes in preparation for separation by gas chromatography. The device includes a conduit that may include two, and sometimes three, separate sections that are connected end-to-end, but which may be separated prior to inserting into a gas chromatograph port. The inner surface of each section is coated with one or more sorbents, each with a different affinity for volatile analytes. The sorbents may be positioned along the sections of the column in order of relative affinity for volatile analytes. The sections may be heated independently of each other to release the volatile analytes from the sorbents more quickly. This device reduces the time and the temperature required to achieve separation by gas chromatography. The device may be used to perform gas chromatography in ubiquitous environments such as the home or a mobile situation.

20 Claims, 6 Drawing Sheets

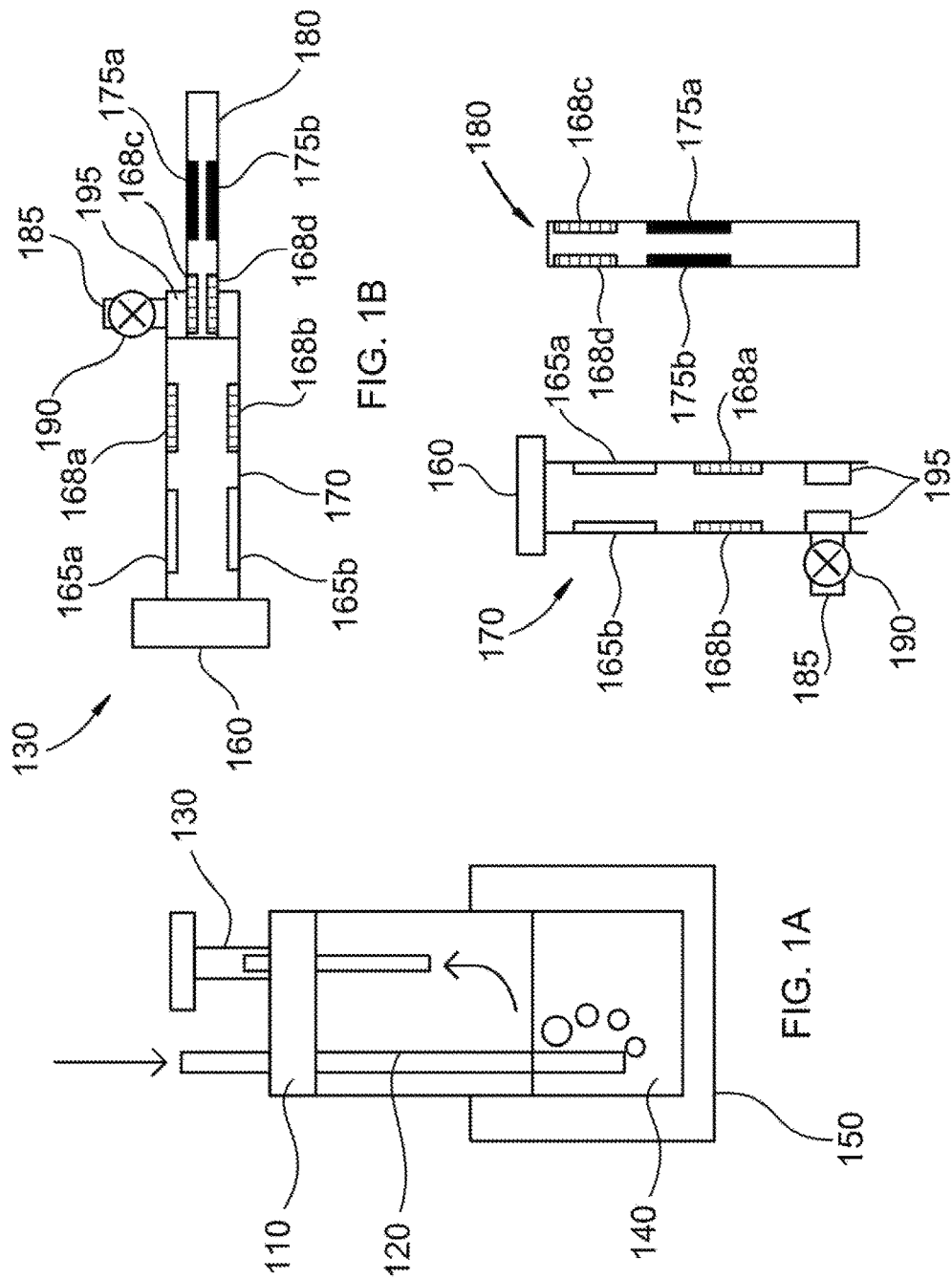

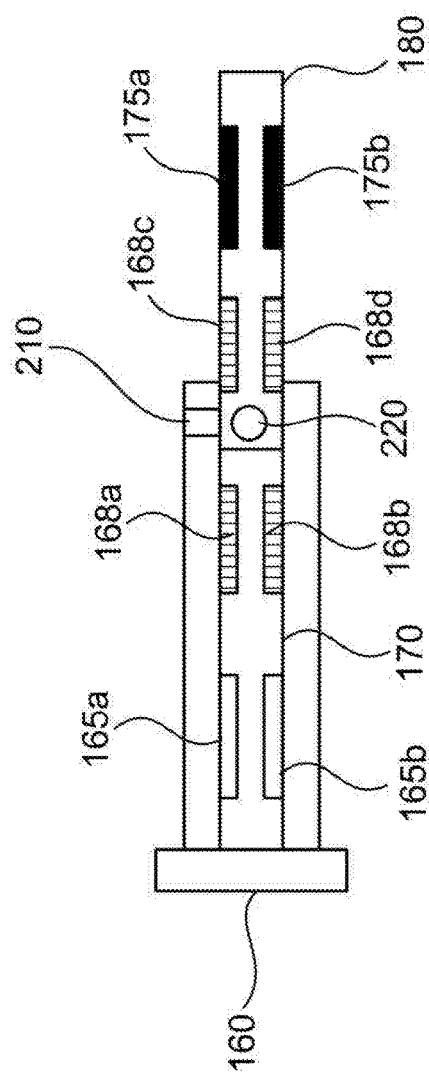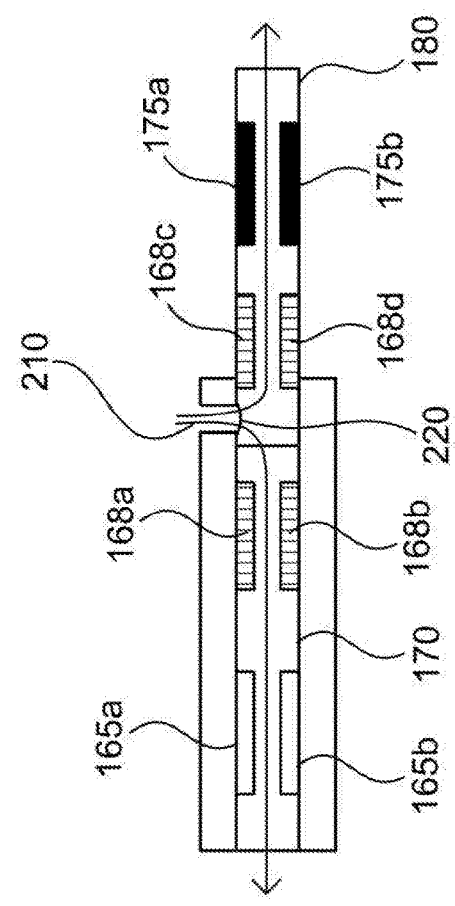

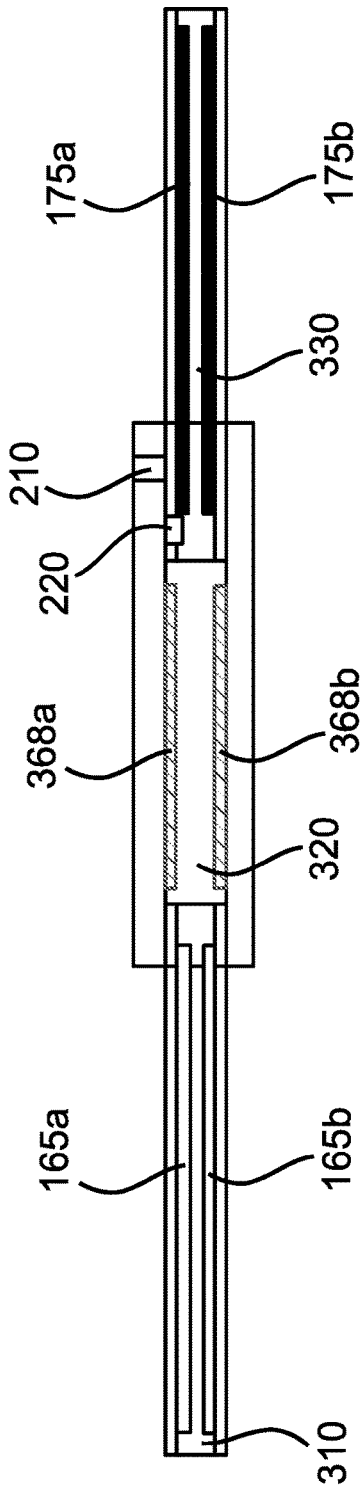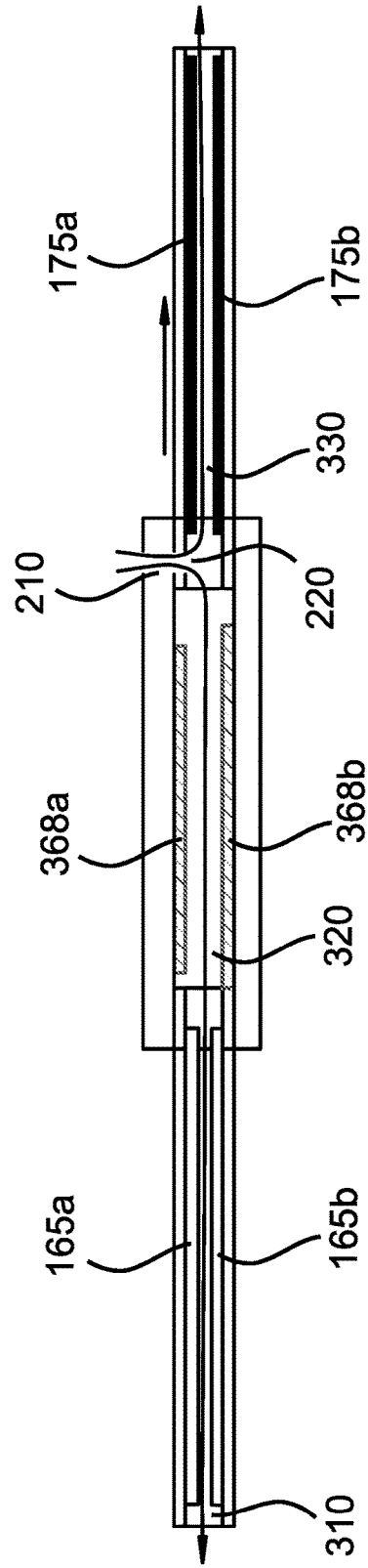
FIG. 3A
FIG. 3B

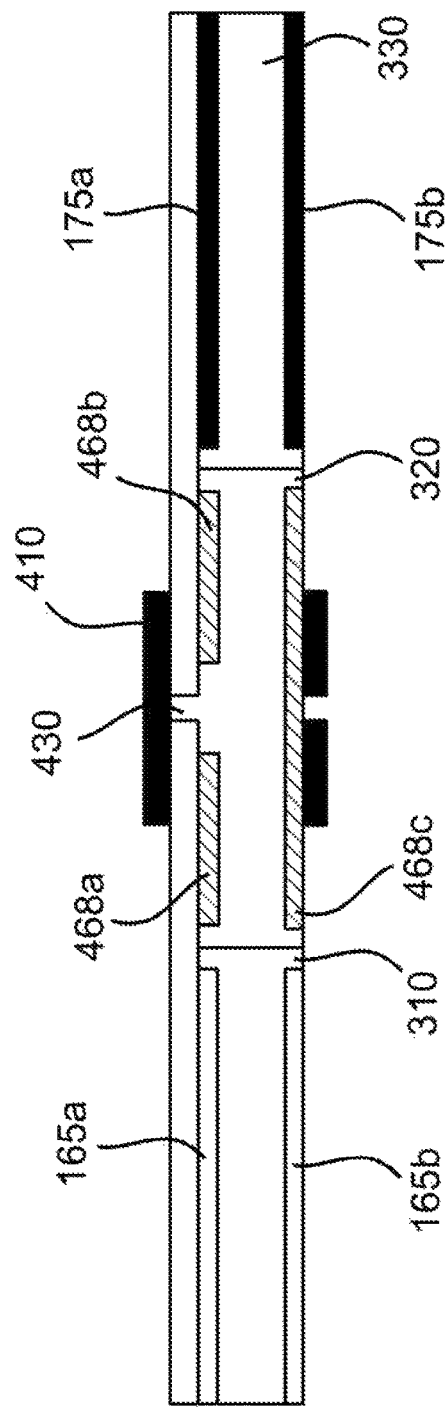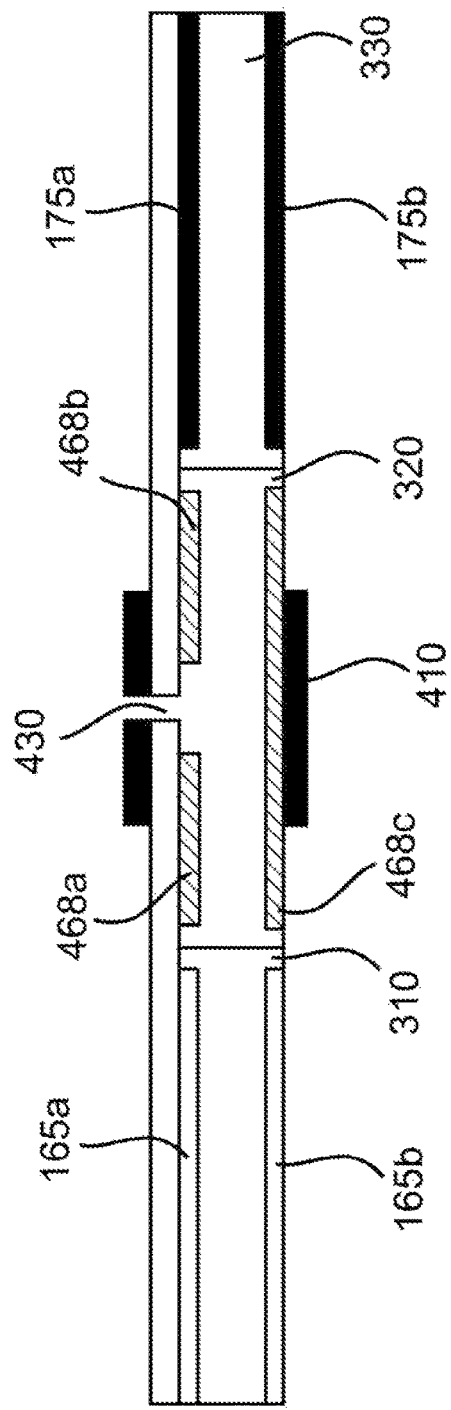

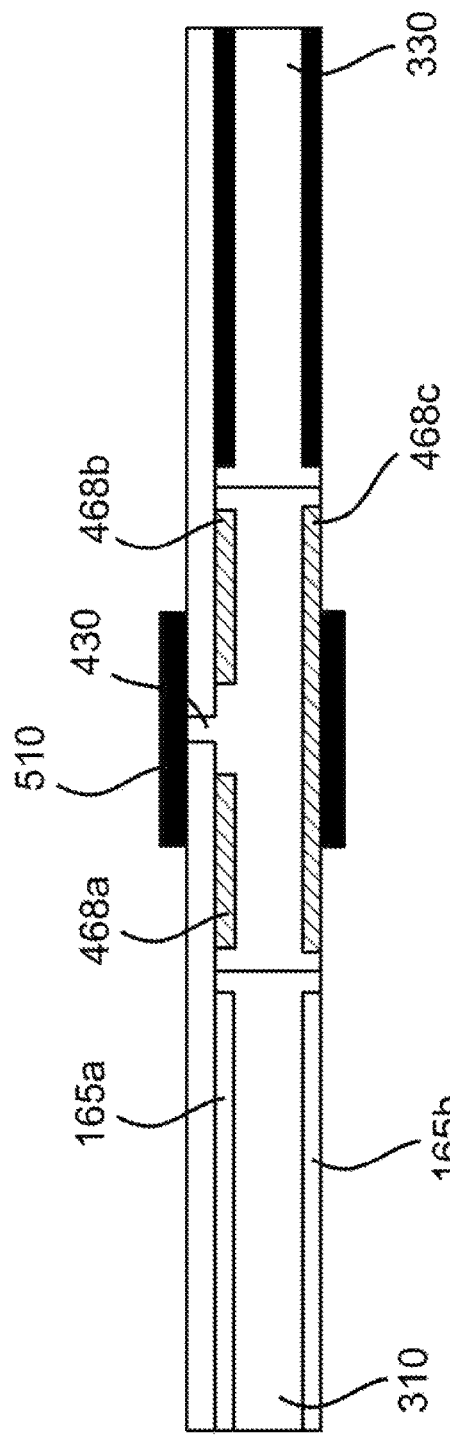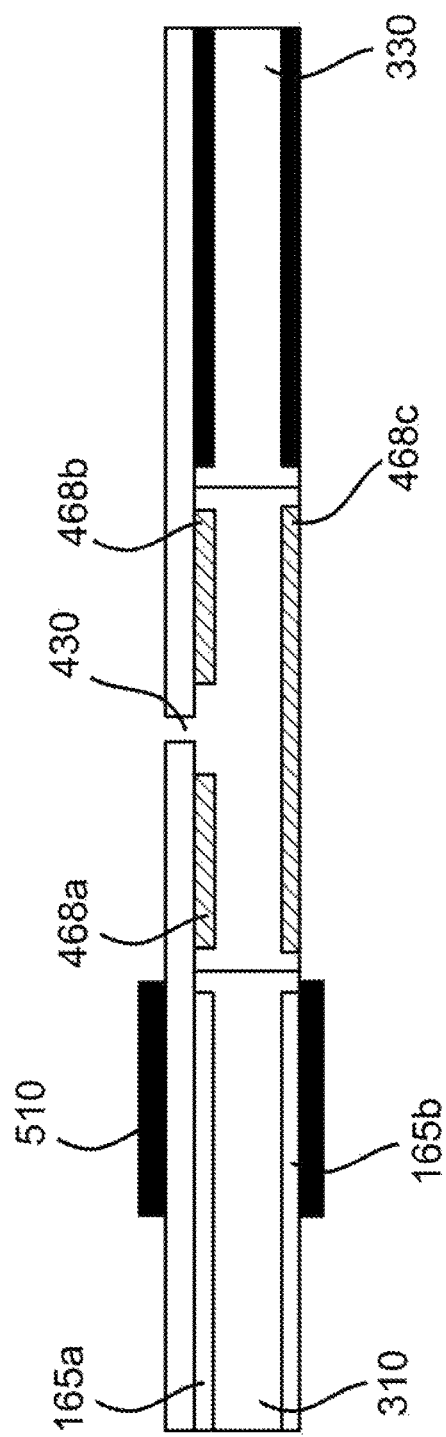

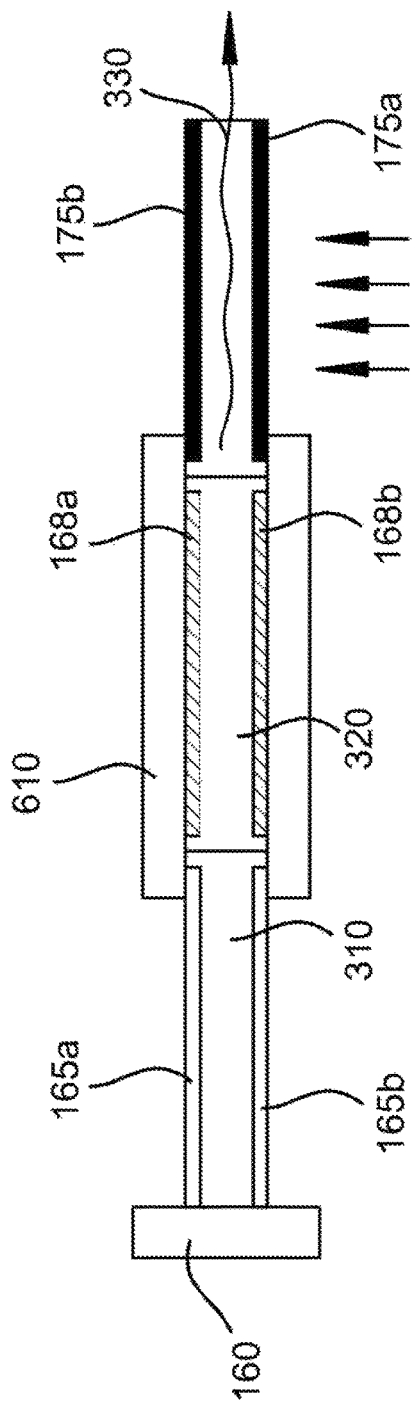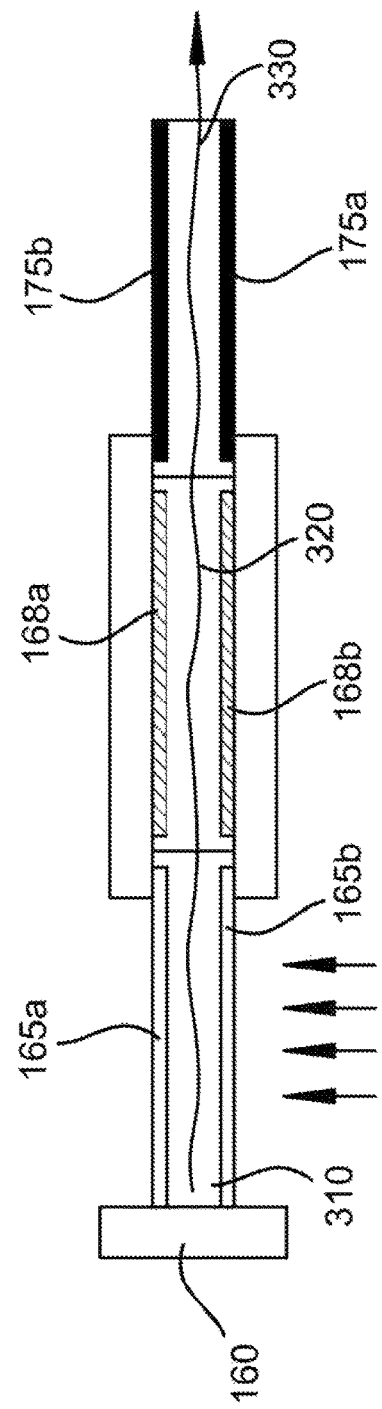
FIG. 6A
FIG. 6B

STAGED PRECONCENTRATION AND PARALLEL COLUMN GAS CHROMATOGRAPHY

BACKGROUND

Field of the Invention

This invention relates to systems and methods for analyzing and separating chemical compounds, particularly using gas chromatography.

Background of the Invention

Sample preparation is required to prior to separation of volatile compounds using gas chromatography (hereinafter, "GC"). First, volatile compounds must be extracted from the sample if the sample is not already gaseous. One such method of extraction of volatile compounds is headspace sampling. In headspace sampling, the sample is heated to promote the evolution of gas phase compounds from the liquid phase into the headspace at the top of the partially filled vial. The second required step is preconcentration which is currently performed by using a sorbent which adsorbs volatile compounds from the sample.

Sparging is a method of combining extraction and preconcentration. In sparging, a gas is bubbled through the liquid sample to promote evolution of volatile compounds from the liquid by Le Chateleir's principal. The bubbled gas passes through a preconcentrator which adsorbs the volatile compounds exhausted from the sample.

Another method for preconcentrating samples for GC is solid phase microextraction (hereinafter, "SPME"). In SPME, a sorbent-coated fiber sheathed in a hollow needle is inserted into the headspace and the fiber is extended into the headspace. The sorbent (or multiple sorbents) on the surface of the fiber constitute the solid phase. The sorbent comes into equilibrium with the volatile compounds in the headspace and is removed from the headspace, the sorbent is heated to eject the adsorbed volatiles into a GC column. It is significant that the partitioning of analytes between the liquid and gas phases in the headspace is related to the concentration of ionic salts in solution which may reduce the solubility of the analytes. Also, different sorbents have different affinities for any given volatile analyte. Consequently, SMPE is not a best practice for quantitative analysis unless care is taken to calibrate the measurement for a particular sample type.

In contrast to SPME, the needle trap technique samples headspace and is quantitative without the need for precalibration. The needle trap moves air from the headspace through a preconcentrator needle in one direction. The inner surface of the preconcentrator needle is typically coated with at least two sorbents of differing affinity for volatile analytes. The flow is then reversed for injection into the gas chromatograph. The needle is heated at relatively high temperatures which causes the sorbents to release the volatile analytes.

The extracted and preconcentrated sample is then separated by GC. This requires a moving phase which comprises an inert gas. Examples of suitable inert gases are nitrogen and helium. The volatile analytes which have a greater affinity for the column walls move more slowly through the column as the mobile phase passes through than those with a lesser affinity for the column walls. The higher affinity volatile analytes may be released more quickly by heating the column. This step reduces the time of the GC run.

It is desirable to adapt GC technology for use in environments outside the laboratory or clinic. The steps of using an inert gas and high temperatures used in conventional techniques present problems with regard to adapting GC to use in a ubiquitous environment, such as a home or in a mobile situation. One is the general lack of an inter mobile phase such as helium or nitrogen gases. A mobile gas chromatograph must either separate oxygen and potential volatile contaminants from the moving phase or run a filtered atmospheric gas mixture through the column. Oxygen may react with both the volatile analytes and the stationary phase of the column at the elevated temperatures necessary to elute analytes with higher affinity to the column in a reasonable amount of time. This has been known to degrade the sample, and sometimes, the column.

Another problem with adapting GC technology to ubiquitous environments is the length of time required to complete separation using standard GC techniques. The length of time required to complete a GC run using current technology may be impractical for the applications in which GC is used in a ubiquitous environment. A solution to address separation of the higher molecular weight volatile analytes that adhere relatively strongly to the GC column is needed to adapt GC technology to a ubiquitous environment.

BRIEF SUMMARY OF THE INVENTION

We disclose a novel device which both extracts and preconcentrates samples in preparation for analysis by GC. The device includes a conduit with at least two sections removably connected to each other in an end-to-end configuration. The inner walls of the sections are coated with sorbents with different affinities for volatile analytes. The sorbents may be positioned within the conduit in order of their binding affinity for volatile analytes. The binding affinity may be based on properties of that include molecular weight and polarity. The device includes an injection port for injecting moving phase gas to desorb the volatile analytes for entry into a gas chromatograph. Openings at each end of the conduit comprise exhaust ports for volatile analytes to exit upon passing a moving phase gas through the conduit. The volatile analytes exit the conduit through each of the exhaust ports in the order of their relative binding affinity to the sorbents. The sections may be separated from each other to exhaust the volatile analytes in each section at different times or using different methods. The conduit may include an injection port through which moving phase gas may be injected into the conduit. The injection port may be positioned at an intersection between sections of the conduit such that moving phase gas travels into the conduit and towards the exhaust ports in both directions from the injection port.

Some embodiments of the device include a thermal insulator positioned between the sections. The thermal insulator prevents heat from traveling between the sections. Thus, one section may be heated to cause the volatile analytes to desorb from the sorbent more quickly without transmitting the heat to the adjacent section.

The disclosed device enables both extraction and preconcentration of samples containing volatile analytes for subsequent analysis by GC. The device results in a faster GC run without the need for the high temperatures required with conventional methods. This device may be used to prepare samples for GC in a ubiquitous setting, including a mobile GC unit or in the home, rather than the laboratory or clinical setting.

BRIEF DESCRIPTION OF THE DRAWINGS

FIG. 1A illustrates an embodiment of the invention during sampling volatile analytes.

FIG. 1B is a close up, cross-sectional view which illustrates an embodiment of the device of FIG. 1A.

FIG. 1C illustrates the embodiment of FIG. 1B separated into two sections.

FIG. 2A is a cross-sectional view which illustrates an embodiment of the device in which the two sections twist to cover the injection port.

FIG. 2B illustrates the embodiment of FIG. 2A in which the two sections have been twisted to expose the injection port.

FIG. 3A is a cross-sectional view which illustrates an embodiment of the device with three sections.

FIG. 3B illustrates the embodiment of FIG. 3A in use.

FIG. 4A is a cross-sectional view which illustrates an embodiment of the device in which the injection port is covered by a rotatable cover.

FIG. 4B illustrates the embodiment of FIG. 4A in which the rotatable cover has been rotated to expose the injection port.

FIG. 5A is a cross-sectional view which illustrates an embodiment of the device in which the injection port is covered by a slidable cover.

FIG. 5B illustrates the embodiment of FIG. 5A in which the slidable cover has been slid to expose the injection port.

FIG. 6A is a cross-sectional view illustrates an embodiment of the device which includes a thermal barrier and in which the second section is being heated.

FIG. 6B illustrates the embodiment of FIG. 6A in which the first section is being heated.

DETAILED DESCRIPTION OF THE INVENTION

Disclosed herein is a staged preconcentration and parallel column for preparing samples for GC. The device both extracts and preconcentrates volatile analytes prior to separation by GC. Specifically, we disclose a conduit that may include at least two sections. Each section may include a proximal and a distal end, an inner surface, and an inner volume. The inner surface of each section may be coated with at least one sorbent. Volatile analytes adsorb to each sorbent with a different affinity. The at least two sections may be linearly connected to each other in an end-to-end configuration creating an intersection between the two sections. For example, a distal end of a first section may be connected to a proximal end of a second section. When joined together, the multiple sections create a single, connected conduit. Gases and fluids may travel through the inner volumes of the multiple sections from one end of the conduit to the other or out through injection ports that may be positioned along the length of the conduit.

The sections may be connected to each other end-to-end using a variety of techniques known in the art. Examples of mechanisms that may be used to connect the sections include, but are not limited to, configurations which allow the distal end of one section and the proximal end of another section to be concentrically nested as well as the use of a friction fit unit or a removable clamp. These connection mechanisms allow the sections to be removed and put back together as needed so that each section may be processed independently of the others to desorb the volatile analytes.

The conduit may further include an injection port through which a moving phase gas may be injected into the device. In some embodiments, the injection port is positioned at the intersection between two sections, for example, at the intersection between a first section and a second section. In such embodiments, the moving phase gas is injected into the conduit approximately at the center of the length of the conduit. The injection port may be in fluid (or gas) communication with the inner volumes of the sections of the conduit. In some embodiments, the injection port is in fluid (or gas) communication with one section but not another. The injection port may include a valve which may be actuated to change which section or sections are in fluid or gas communication with the injection port at a given time.

The device may include two or more exhaust ports. Some embodiments include two exhaust ports. In such embodiments, the first exhaust port is defined by an opening in the proximal end of the first section and the second exhaust port is defined by an opening in the distal end of the second section. Consequently, the exhaust ports are at each end of the conduit.

In some embodiments, in which the injection port is located at an intersection between two sections, the injection port is created by aligning two orifices, each in a wall of a section of the conduit. In an embodiment that includes two sections, the first orifice may be at the distal end of the first section and the second orifice may be at the proximal end of the second section. In these embodiments, the first and second sections are connected at the distal end of the first section and the proximal end of the second section. The two sections may rotate relative to each other (twist) so that when the two orifices line up, they create an open injection port. In contrast, when the sections are rotated such that the two orifices do not line up, the port is closed. In the latter position, there is no orifice through which sample may be injected or undesirably escape.

Additionally, the injection port may be opened and closed through other mechanisms. Some embodiments include a cover that slides longitudinally along the length of the conduit. The cover includes a sleeve that covers and uncovers the injection port as the cover slides longitudinally along the conduit. The sleeve slides over the injection port to close it and slides away from the injection port to open it.

In another embodiment the conduit includes a rotatable cover. This cover includes an opening on one side of the cover. The cover fits around the conduit and rotates around the conduit like a ring twisting around a finger. When the opening in the cover is positioned over the injection port, the injection port is open. The user need only rotate the cover further to move the opening in the cover around the conduit and away from the injection port. With the cover in this position, the injection port is covered, and, consequently, closed.

The inner surface of each section of the conduit may be coated with at least one sorbent to which volatile analytes bind with a different affinity. The sorbents may be coated within the conduit in order of increasing or decreasing affinity to volatile analytes. For example, in a two-section conduit, the first section may have the weaker binding sorbent and the second section may have the stronger binding sorbent. In some embodiments, there may be a center section made of the distal end of the first section and the proximal end of the second section that is coated with an intermediate affinity sorbent. In this embodiment, the three sorbents are positioned such that they increase in binding affinity moving along the conduit from the first to the second section. Thus, when the adhered volatile analytes are removed and enter the gas chromatograph, they do so in order of their relative possession of specific molecular properties. Furthermore, in some embodiments, the injection port transverses center section and the intermediate sorbent.

The specific molecular properties that result in different binding affinities include molecular weight and polarity. For example, in some embodiments, each sorbent adheres to different volatile analytes based on their polarity. When the sorbents are placed along the column in order of their affinity for more polar compounds, the volatile analytes bind along the column in order of their relative polarity and then are released into the gas chromatograph in order of their relative polarity. Similarly, the volatile analytes may adhere to the sorbents according to their size (molecular weight). They will both adhere and then be released in order of relative molecular weight.

When in use, the moving phase may be injected into the injection port of a conduit that has been loaded with sample. In embodiments in which the injection port is positioned in a center section or at the intersection between a first and a second section, the moving phase gas travel toward both ends of the conduit and out each exhaust port. As the moving phase passes through the conduit and over the sorbents, the volatile analytes desorb into the moving phase. At least in part, because of the order of placement of the sorbents (according to relative binding affinity to volatile analytes), the more polar analytes may exit through the exhaust port at one end of the conduit and the less polar analytes may exit through the exhaust port at the other end of the conduit. Alternatively, the higher molecular weight molecules may exit through the exhaust port at one end of the conduit and the lower molecular weight molecules may exit through the exhaust port at the other end of the conduit. Alternatively, the sections may be mechanically separated from each other and the volatile analytes may be removed by passing a moving phase through each section separately.

Volatile analytes may be encouraged to desorb by heating the conduit or sections thereof. The mechanically separated sections may be heated independently. Some embodiments include thermal insulation which may be positioned between sections of the conduit. In some embodiments, the thermal insulation is positioned adjacent to the conduit at a center section or intersection. By placing the thermal insulation between sections, the thermal insulation inhibits heat transfer between the sections. Consequently, a heater that may be connected to the conduit may independently heat one section or the other to provide greater control of the rate at which the volatile analytes desorb from the sorbents.

Some embodiments include a third section that may be mechanically separated from the first and second section. The third section may be positioned between the first and second sections. The inner surface of the third section may be coated with an intermediate sorbent, the intermediate sorbent having a binding affinity for volatile analytes between that of the first section and the second section. The first, second, and third sections may be removably connected to each other in an end-to-end manner through mechanisms described with regard to the two-section conduit.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Referring now to the drawings, FIG. 1A illustrates how an embodiment of the invention may be loaded with volatile analytes. An embodiment of the invention, device 130, is inserted through septum 110 which covers a vial. Device 130 comprises a conduit with two sections. The vial contains sample 140 which is in liquid form and contains volatile analytes. Tubing 120 is also inserted through septum 110 and a gas is injected into the vial as illustrated by the arrow pointing down into tubing 120. While FIG. 1A shows the gas being injected into sample 140, the gas may alternatively be injected into the headspace. The gas causes volatile analytes to become gaseous and travel into device 130 through the conduit. The vial may also be heated by heater 150 to encourage the volatile analytes to change from liquid to gas phase.

FIG. 1B illustrates a cross-sectional view of device 130 in more detail. Device 130 includes handle 160 which is placed on a proximal end of first section 170 of the conduit. Second section 180 of the conduit is connected end-to-end to first section 170 by concentrically nesting the two sections. The inner surfaces of each section are coated with sorbents, each possessing different volatile analyte binding affinities. The embodiment of FIG. 1B includes a low molecular weight binding sorbent 165a and 165b (shown in white), intermediate molecular weight binding sorbent 168a, 168b, 168c, and 168d (shown hatched), and high molecular weight binding sorbent 175a and 175b (shown in black). FIG. 1B also illustrates injection port 185 which is positioned at central section 195 of device 130. Injection port 185 includes valve 190 which may be opened and closed to allow mobile phase gas to be injected into the conduit.

FIG. 1C illustrates device 130 with first section 170 mechanically separated from second section 180. By mechanically separating the two sections, the volatile analytes may be desorbed from their respective sections using different techniques which may include different moving phase gases or different temperatures.

FIG. 2A illustrates an embodiment of the disclosed device which is a modification of device 130. Specifically, FIG. 2A illustrates first orifice 210 on first section 170 and second orifice 220 on second section 180. When aligned, first orifice 210 and second orifice 220 form a continuous channel which functions as an injection port for movable phase gas. First section 170 and second section 180 rotate, or twist, relative to each other so that first orifice 210 and second orifice 220 are sometimes in line with each other forming a continuous channel and sometimes not aligned so that the channel is blocked. In FIG. 2A, first orifice 210 and second orifice 220 are not aligned so that the injection port is closed. This may be the preferred position when the device is being loaded with sample.

FIG. 2B illustrates the device of FIG. 2A after first section 170 and second section 180 have been rotated such that first orifice 210 and second orifice 220 align to form a continuous channel. A moving phase gas may be injected through the injection port formed by first orifice 210 and second orifice 220 to exhaust the volatile analytes into a gas chromatograph. The arrows in FIG. 2B illustrate the movement of a moving phase gas as it is injected through the injection port and diverted through both first section 170 and second section 180 and out their respective exhaust ports.

FIGS. 3A and 3B illustrate yet another embodiment in which the injection port is opened and closed by sliding second section 330 laterally along the conduit to bring first orifice 210 and second orifice 220 in and out of alignment. FIG. 3A illustrates the device in a position in which first orifice 210 and second orifice 220 are not aligned and, therefore, do not form a continuous channel to create an open injection port. FIG. 3B illustrates the embodiment of FIG. 3A in which second section 330 has been slid to the right (direction of movement shown by the arrow above second section 330). In this position, first orifice 210 and second orifice 220 are aligned forming an open injection port. Arrows within the conduit illustrate the movement of moving phase gas through the injection port and through the conduit in both directions. The moving phase causes the volatile analytes that adsorbed to the three sorbents to desorb and move out of the device through the two exhaust ports.

The embodiment shown in FIGS. 3A and 3B includes first section 310 and second section 330, similar to the embodiment illustrated in FIGS. 2A and 2B. The embodiment of FIGS. 3A and 3B further includes third section 320. The inner surface of third section 320 is coated with intermediate sorbent 368a and 368b (shown hatched). Intermediate sorbent 368a and 368b possess a binding affinity for volatile analytes that is between that of low molecular weight binding sorbent 165a and 165b (shown in white) and high molecular weight binding sorbent 175a and 175b (shown in black). Specifically, intermediate sorbent 368a and 368b binds volatile analytes that have a molecular weight that is between those bound by low molecular weight binding sorbent 165a and 165b and high molecular weight binding sorbent 175a and 175b.

FIGS. 4A and 4B illustrate yet another embodiment of the device in which rotatable cover 410 opens and closes injection port 430. The embodiment illustrated in FIGS. 4A and 4B includes first section 310, second section 330, and third section 320. First section 310 includes low molecular weight binding sorbent 165a and 165b (shown in white), second section 330 includes high molecular weight binding sorbent 175a and 175b (shown in black), and third section 320 includes intermediate sorbent 468a, 468b, and 468c (shown hatched) which binds volatile analytes that have a molecular weight that is between those bound by low molecular weight binding sorbent 165a and 165b and high molecular weight binding sorbent 175a and 175b. Injection port 430 is positioned within third section 320 and is between intermediate sorbent 468a and 468b.

FIGS. 4A and 4B further illustrate rotatable cover 410 which surrounds third section 320. Rotatable cover 410 rotates (twists) around third section 320 like a ring twisting around a finger. Rotatable cover 410 further includes an orifice. FIG. 4A illustrates rotatable cover 410 in a position in which the orifice does not align with injection port 430. In this position, rotatable cover 410 covers injection port 430 preventing contents of the column from escaping through injection port 430 and preventing contaminants from entering.

In FIG. 4B, rotatable cover has been rotated around third section 320 to a position in which the orifice in rotatable cover 410 is aligned with injection port 430. In this position, injection port 430 is open to receive movable phase gas.

FIGS. 5A and 5B illustrate an embodiment similar to that of FIGS. 4A and 4B except that slidable cover 510 is used to expose and cover injection port 430. Slidable cover 510 is positioned around the circumference of the conduit and slides laterally along the conduit (left to right in the drawings). FIG. 5A illustrates slidable cover 510 in a first position in which it covers injection port 430. FIG. 5B illustrates slidable cover 510 in a second position, specifically, slid to the left to encircle first section 310. Because slidable cover 510 has moved away from injection port 430, it no longer blocks access to injection port 430. Moving phase gas may be injected into injection port 430 when slidable cover 510 is in this position.

FIGS. 6A and 6B illustrate an embodiment of the device showing how heat may be used to differentially desorb volatile analytes which are adsorbed to sorbents in different sections of the conduit. Vertical arrows indicate heat in the drawings. In FIG. 6A, heat is being applied to second section 330 which includes high molecular weight binding sorbent 175a and 175b. Note that heat is not applied to other sections of the conduit in FIG. 6A. The heat causes the higher molecular weight volatile analytes to desorb more quickly than they would at a lower temperature. The higher molecular weight analytes then move out of the conduit through the exhaust port as illustrated by the wavy arrow.

FIG. 6B illustrates the device of FIG. 6A in which heat is now being applied to first section 310 (again as shown by vertical arrows). The heat causes low molecular weight volatile analytes to desorb from low molecular weight binding sorbent 165a and 165b. The low molecular weight volatile analytes then move through the full length of the conduit and through the exhaust port in second section 330 as shown by the wavy arrow. This design enables the user to sequentially desorb volatile analytes of different molecular weights.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A device for extracting and preconcentrating volatile analytes prior to gas chromatography comprising:
    a conduit through which volatile analytes flow comprising:
        a first section, the first section comprising a first inner volume, a first inner surface, a first proximal end, and a first distal end;
        a second section, the second section comprising a second inner volume, a second inner surface, a second proximal end, and a second distal end, wherein the first distal end is removably connected to the second proximal end at an intersection, and wherein the first section is positioned linearly in relation to the second section;
    a first sorbent, wherein the first sorbent comprises a first analyte-binding affinity, and wherein the first sorbent coats at least a portion of the first inner surface;
    a second sorbent, wherein the second sorbent comprises a second analyte-binding affinity, wherein the second sorbent coats at least a portion of the second inner surface; and
    an injection port.

2. The device of claim 1, wherein the injection port is positioned at the intersection.

3. The device of claim 2, wherein the injection port is in fluid communication with one or both of the first inner volume and the second inner volume.

4. The device of claim 1, wherein the injection port comprises a valve.

5. The device of claim 1, further comprising a first exhaust port and a second exhaust port.

6. The device of claim 5, wherein the first exhaust port is defined by a first opening in the first proximal end and the second exhaust port is defined by a second opening in the second distal end.

7. The device of claim 1, further comprising a thermal insulator, wherein the thermal insulator is positioned adjacent to one or more of the first inner surface and the second inner surface at the intersection, and wherein the thermal insulator inhibits heat transfer between the first section and the second section.

8. The device of claim 1, wherein the first sorbent comprises a greater affinity for polar molecules than does the second sorbent.

9. The device of claim 1 wherein the first sorbent comprises a greater affinity for higher molecular weight molecules than does the second sorbent.

10. The device of claim 1, wherein the first distal end and the second proximal end removably and concentrically nest.

11. The device of claim 1, wherein the first distal end and the second proximal end are removably joined through a friction fit union.

12. The device of claim 1, wherein the first distal end and the second proximal end are joined by a removable clamp.

13. The device of claim 1, wherein the injection port comprises a first orifice in the first distal end and a second orifice in the second proximal end, and wherein the first section and the second section rotate to align the first orifice and the second orifice thereby defining the injection port.

14. The device of claim 1, further comprising a center section and an intermediate sorbent, wherein the center section comprises one or more of the following:
   at least a portion of the first distal end, the at least a portion of the first distal end comprising a distal portion of the first inner surface, and
      at least a portion of the second proximal end, the at least a portion of the second proximal end comprising a proximal portion of the second inner surface;
      wherein the intermediate sorbent coats one or more of the distal portion of the first inner surface and the proximal portion of the second inner surface,
   wherein the intermediate sorbent is positioned between the first sorbent and the second sorbent,
   wherein the intermediate sorbent comprises an intermediate analyte-binding affinity, and
      wherein the intermediate analyte-binding affinity is at a level that is intermediate to the first analyte-binding affinity and the second analyte-binding affinity.

15. The device of claim 14, wherein the injection port transverses center section and the intermediate sorbent.

16. The device of claim 1, further comprising a third section comprising:
   a third inner volume;
   a third inner surface, wherein the third inner surface is coated with an intermediate sorbent, wherein the intermediate sorbent comprises an intermediate analyte-binding affinity, and wherein the intermediate analyte-binding affinity is at a level that is intermediate to the first analyte-binding affinity and the second analyte-binding affinity;
   a third proximal end; and
   a third distal end,
   wherein the first distal end and the third proximal end nest concentrically, and wherein the second proximal end and the third distal end nest concentrically.

17. The device of claim 16, wherein the injection port is positioned on the third section.

18. The device of claim 17, further comprising a slideably attached cover, the slideably attached cover comprising a sleeve, wherein the sleeve covers and uncovers the injection port as the cover slides longitudinally along the conduit.

19. The device of claim 17, further comprising a rotatable cover, wherein the rotatable cover is positioned over the injection port, and wherein the rotatable cover comprises an opening that rotates over and uncovers the injection port.

20. The device of claim 16, wherein the center section comprises a thermal insulator, and wherein the thermal insulator inhibits heat transfer between the first section and the second section.

* * * * *